(12) United States Patent
Bjorling et al.

(10) Patent No.: US 10,195,541 B2
(45) Date of Patent: Feb. 5, 2019

(54) METHOD FOR TRANSFERRING SLURRY

(71) Applicant: GE Healthcare Bio-Sciences AB, Uppsala (SE)

(72) Inventors: Mikael Bjorling, Uppsala (SE); Bengt Niklas Edblad, Uppsala (SE); Per Karlberg, Uppsala (SE); Jonas Karlsson, Uppsala (SE); Joakim Lundkvist, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 25 days.

(21) Appl. No.: 15/023,972

(22) PCT Filed: Sep. 26, 2014

(86) PCT No.: PCT/SE2014/051107
§ 371 (c)(1),
(2) Date: Mar. 22, 2016

(87) PCT Pub. No.: WO2015/047172
PCT Pub. Date: Apr. 2, 2015

(65) Prior Publication Data
US 2016/0228790 A1 Aug. 11, 2016

(30) Foreign Application Priority Data

Sep. 30, 2013 (SE) ...................................... 1351136

(51) Int. Cl.
*B01D 15/10* (2006.01)
*B01D 15/20* (2006.01)
*G01N 30/56* (2006.01)

(52) U.S. Cl.
CPC ............ *B01D 15/206* (2013.01); *G01N 30/56* (2013.01); *G01N 2030/565* (2013.01)

(58) Field of Classification Search
CPC ...... B01D 15/206; G01N 30/56; G01N 30/565
(Continued)

(56) References Cited

U.S. PATENT DOCUMENTS 3,879,179 A 4/1975 Chinnock et al.
5,651,399 A * 7/1997 Holland ................. H01M 4/26
141/1.1
(Continued)

FOREIGN PATENT DOCUMENTS

CN 101622044 A 1/2010
CN 101631600 A 1/2010
(Continued)

OTHER PUBLICATIONS

Office Action received for Chinese Patent Application No. 201480053773.4, dated Jan. 20, 2017, 24 pages. (13 pages English translation + 11 pages Official Copy).
(Continued)

*Primary Examiner* — Nicolas A Arnett
(74) *Attorney, Agent, or Firm* — Wood IP LLC

(57) ABSTRACT

A method and a slurry tank system for transferring chromatography media slurry from a slurry tank (3) to a chromatography column (9), said method comprising monitoring the content of slurry in the slurry tank (3) during the transferring and controlling the transferring of the slurry to the column (9) in dependence of the content of slurry in the slurry tank (3).

25 Claims, 2 Drawing Sheets

(58) Field of Classification Search
USPC ..................................... 210/143, 198.2, 656
See application file for complete search history.

(56) References Cited

U.S. PATENT DOCUMENTS

| | | | | |
|---|---|---|---|---|
| 6,347,650 B1* | 2/2002 | Affleck | ............... | B65B 1/38 141/1 |
| 6,966,991 B2* | 11/2005 | Hofmann | ............ | B01D 15/206 210/198.2 |
| 7,135,107 B2* | 11/2006 | Palmer | ............... | B01D 21/0045 210/104 |
| 7,402,251 B2* | 7/2008 | Mann | ............... | B01D 15/206 210/198.2 |
| 7,435,350 B2* | 10/2008 | Noyes | ............... | B01D 15/206 210/198.2 |
| 7,452,471 B2* | 11/2008 | Windahl | ............ | B01D 15/206 210/143 |
| 8,066,882 B2* | 11/2011 | Edblad | ............... | B01D 15/206 210/143 |
| 8,092,073 B2* | 1/2012 | Asplund | ............ | B01F 3/188 366/136 |
| 8,114,295 B2* | 2/2012 | Noyes | ............... | B01D 15/206 210/198.2 |
| 8,117,901 B2* | 2/2012 | Svensson | ............ | B01D 15/206 73/53.01 |
| 8,133,395 B2* | 3/2012 | Karlsson | ............ | B01D 15/206 210/143 |
| 8,454,834 B2* | 6/2013 | Karlberg | ............ | B01D 15/206 210/143 |
| 8,607,829 B2* | 12/2013 | Williams | ............ | B01D 15/206 141/12 |
| 8,778,187 B2* | 7/2014 | Gebauer | ............ | B01D 15/206 210/198.2 |
| 9,116,150 B2* | 8/2015 | Natarajan | ............ | G01N 30/56 |
| 9,274,092 B2* | 3/2016 | Natarajan | ............ | G01N 30/56 |
| 9,597,610 B2* | 3/2017 | Gebauer | ............ | B01D 15/206 |
| 9,597,611 B2* | 3/2017 | Gebauer | ............ | B01D 15/206 |
| 2006/0219616 A1* | 10/2006 | Noyes | ............... | B01D 15/206 210/198.2 |
| 2007/0090053 A1* | 4/2007 | Windahl | ............... | B01D 15/206 210/656 |
| 2008/0217248 A1* | 9/2008 | Gebauer | ............ | B01D 15/206 210/656 |
| 2009/0007643 A1 | 1/2009 | Svensson et al. | | |
| 2009/0014389 A1* | 1/2009 | Noyes | ............... | B01D 15/206 210/656 |
| 2009/0038381 A1* | 2/2009 | Windahl | ............... | B01D 15/206 73/61.56 |
| 2010/0084341 A1* | 4/2010 | Mann | ............... | B01D 15/206 210/656 |
| 2010/0084342 A1* | 4/2010 | Natarajan | ........... | G01N 30/56 210/656 |
| 2010/0313992 A1* | 12/2010 | Williams | ............ | B01D 15/206 141/1 |
| 2011/0053127 A1* | 3/2011 | Karlberg | ............ | B01D 15/206 434/219 |
| 2011/0073213 A1* | 3/2011 | Edblad | ............... | B01D 15/206 141/1 |
| 2011/0077766 A1* | 3/2011 | Karlsson | ............ | B01D 15/206 700/110 |
| 2011/0100932 A1* | 5/2011 | Lonnqvist | ........... | B01D 15/20 210/803 |
| 2011/0139689 A1 | 6/2011 | Snyder | | |
| 2012/0073698 A1* | 3/2012 | Edblad | ............... | B01D 15/206 141/1 |
| 2013/0061941 A1* | 3/2013 | Gebauer | ............ | B01D 15/206 137/15.01 |
| 2013/0263968 A1* | 10/2013 | Karlberg | ............ | B01D 15/206 141/1 |
| 2014/0076459 A1* | 3/2014 | Williams | ............ | B01D 15/206 141/12 |
| 2015/0346169 A1* | 12/2015 | Natarajan | ........... | G01N 30/56 141/12 |
| 2017/0097326 A1* | 4/2017 | Liu | ............... | G01N 30/56 |
| 2017/0182432 A1* | 6/2017 | Gebauer | ............ | B01D 15/206 |

FOREIGN PATENT DOCUMENTS

| | | |
|---|---|---|
| CN | 102047107 A | 5/2011 |
| CN | 102077087 A | 5/2011 |
| EP | 1710005 A1 | 10/2006 |
| EP | 2175268 A1 | 4/2010 |
| EP | 3052931 A1 | 8/2016 |
| JP | 06066779 A | 3/1994 |
| JP | 2010520485 A | 6/2010 |
| JP | 2010520992 A | 6/2010 |
| JP | 2011522248 A | 7/2011 |
| JP | 2011525988 A | 9/2011 |
| JP | 2012159462 A | 8/2012 |
| KR | 101015284 B1 | 2/2011 |
| WO | 2007/045191 A2 | 4/2007 |
| WO | 2008109192 A1 | 9/2008 |
| WO | 2009/093953 A1 | 7/2009 |
| WO | 2009/157853 A1 | 12/2009 |
| WO | 2015/047172 A1 | 4/2015 |

OTHER PUBLICATIONS

International Preliminary Report on Patentability received for PCT Patent Application No. PCT/SE2014/051107, dated Apr. 5, 2016, 6 pages.
Extended European Search Report Received for European Patent Application No. 14849428.9, dated Apr. 11, 2017, 7 pages.
International Search Report and Written Opinion regarding International Application No. PCT/SE2014/051107, dated Nov. 20, 2014, 11 pages.
Japan Notice of Preliminary Rejection for Japanese Patent Application No. 2016-518082, dated Jul. 24, 2018, 5 pages.

* cited by examiner

METHOD FOR TRANSFERRING SLURRY

CROSS-REFERENCE TO RELATED APPLICATIONS

This application is a filing under 35 U.S.C. 371 of international application number PCT/SE2014/051107, filed Sep. 26, 2014, which claims priority to Swedish application number SE 1351136-5, filed Sep. 30, 2013, the entire disclosures of each of which are hereby incorporated by reference.

FIELD OF THE INVENTION

The present invention relates to a method for transferring chromatography media slurry from a slurry tank to a chromatography column, to a slurry tank system and to a control system in said slurry tank system.

BACKGROUND OF THE INVENTION

Columns used in liquid chromatography typically comprise a tubular body enclosing a packed bed of porous chromatography medium through which a carrier liquid flows, with separation taking place by material collection between the carrier liquid and solid phase of the porous medium. Typically, the medium is enclosed in the column as a packed bed formed by consolidating a suspension of discrete particles, known as slurry that is pumped, poured, or sucked into the column. Consolidation of the slurry into a consolidated packed bed is achieved by compressing the slurry so that it is packed into a volume, which is less than the volume that it would have occupied if it had been allowed to settle under the influence of gravity to form a sedimented bed. The efficiency of subsequent chromatographic separation relies strongly on 1) the liquid distribution and collection system at the fluid inlet and outlet of the packed bed, 2) on the spatial orientation (also know as the packing geometry) of the media particles in the packed bed, and 3) on the compression of the packed bed. If the compression of the packed bed is too low then chromatographic separations performed on that bed suffer from "tailing" and, generally, such insufficiently compressed beds are unstable. If the compression of the packed bed is too high then chromatographic separations performed by the bed suffer from "leading" and such over-compressed beds can affect throughput and binding capacity, and, in general, give much higher operating pressures. If the compression is optimum, then the separation peaks formed during use exhibit much less leading or tailing and are substantially symmetrical. The optimum degree of compression required for a column is determined experimentally for each column size (width or diameter), bed height, and media type.

Prior to any separation process, the bed has to be prepared by starting from the slurry of particles that has to be introduced into the column. The process of bed formation is called 'the packing procedure' and a correctly packed bed is a critical factor influencing the performance of a packed bed. One of the primary goals of the packing procedure is to provide a bed, which is compressed by the optimum amount of compression, i.e. the optimum compression factor. The height of the bed which often is user defined when it is optimally compressed is called the target compressed bed height.

Large-scale columns can be prepared by suctioning or injecting into the column a predetermined volume of slurry having a specified concentration of media particles. Once the predetermined volume of slurry has been delivered into the column it needs to be consolidated and compressed. This can be accomplished for example by moving a movable adapter down the longitudinal axis of the column towards the bottom of the column, normally at a constant speed push both liquid and particles towards the bottom of the column. The excess liquid during this procedure is expelled at the column outlet, while the media particles are retained by means of a filter material, a so-called 'bed support', with pores too small to allow the media particles to pass through. The packing process is complete once the packed bed has been compressed by the optimum degree of compression. There are alternative ways of packing. For example a flow can be applied to force the particles in the slurry to move towards the outlet of the column instead of moving an adapter downwards. A further alternative is to use spray nozzles spraying in slurry until a packed bed is achieved. The packing process is considered successful if the compressed bed allows for a good and robust chromatographic performance. However, packing such an optimally compressed bed of chromatography media in a chromatography column by manual means is not easy to accomplish in practice due to the fact that the quality of the final packed bed depends to a great extent on the skill of the operator. During filling and subsequent packing of the column, the operator manually selects and adjusts all packing parameters such as valve positions, pump speed, adapter's speed of movement, etc. The operator has to measure the slurry concentration in order to decide how much slurry that should be filled into the column. If the measure of the slurry concentration is not exact (which is often the case because it is hard to measure the slurry concentration exactly) the volume of the slurry filled into the column is not optimal and the consolidated bed will settle at a bed height that was not expected (as calculated from the measured slurry concentration) and hereby the target packing factor can not be achieved at target bed height. Furthermore, the operator also has to judge the point when the adapter starts compressing the bed. This point is used to calculate how much further the adapter must move in order to obtain the required amount of compression. Mistakes in the selection of any of the packing parameters normally lead to an under performing column. Further, in columns equipped with a transparent tube it may be difficult, and in columns equipped with a non-transparent tube such as stainless steel it is impossible, to judge by eye when compression of the bed actually starts and a significant error at this point makes it impossible to obtain an optimally compressed bed.

There is also a risk of damaging the media and the column if the user takes wrong decisions.

The chromatography media slurry is provided to the chromatography column from a slurry tank. The chromatography media is expensive and it would be advantageous if all the slurry present in the tank could be transferred to the column. However, the introduction of air into the column needs to be avoided. Air in the column could adversely affect the chromatography performance.

Therefore, there is a need for a system and method for the improved transferring of slurry from the slurry tank to the chromatography column.

SUMMARY OF THE INVENTION

An object of the invention is to provide a slurry transferring method and system where as much as possible of the slurry in the slurry tank is used when packing a chromatography column and the risk of introducing air into the column is minimized.

A further object of the invention is to provide a fully automated method for the transferring of slurry into the chromatography column that ensures good use of the slurry and no risk of introducing air into the column.

This is achieved in a method according to claim 1, in a slurry tank system according to claim 10 and in a control system according to claim 19.

Hereby the transferring of slurry is made dependent of the content of slurry in the tank. Therefore it will be possible to use more of the slurry without the risk of introducing air into the column.

In one embodiment of the invention the transferring of slurry to a column and the monitoring of the content in the slurry tank is performed automatically by a control system.

In one embodiment of the invention the controlling of the transfer of the slurry to the column comprises stopping the transferring of slurry, when the slurry content is below a predefined threshold level. Hereby the risk that air will be introduced into the column is very small.

In one embodiment of the invention the controlling of the transfer of the slurry to the column comprises decreasing the transferring speed when the slurry content is below a predefined threshold level. Hereby the risk of introducing air into the column is even more decreased and the possibility to control the transferring of slurry is improved.

In one embodiment of the invention inside walls of the slurry tank are rinsed by spraying a liquid or a gas into the slurry tank when the slurry content is below a predefined threshold level. Hereby any remaining media on the inside walls of the slurry tank can also be used and no media is wasted.

In one embodiment of the invention the monitoring comprises measuring slurry level in the slurry tank or measuring weight of the slurry tank.

In another embodiment the monitoring comprises measuring air content in a transferring tube used for the transferring of the slurry from the slurry tank to the chromatography column.

In one embodiment of the invention transferring slurry from the slurry tank to the chromatography column is performed by raising an adaptor in the chromatography column.

BRIEF DESCRIPTION OF THE DRAWINGS

These and other advantages of the present invention will become more apparent as the following description is read in conjunction with the accompanying drawings, wherein.

DETAILED DESCRIPTION OF THE INVENTION

The presently preferred embodiments of the invention are described with reference to the drawings. The descriptions of the preferred embodiments are exemplary and are not intended to limit the scope of the invention.

Figure 1:
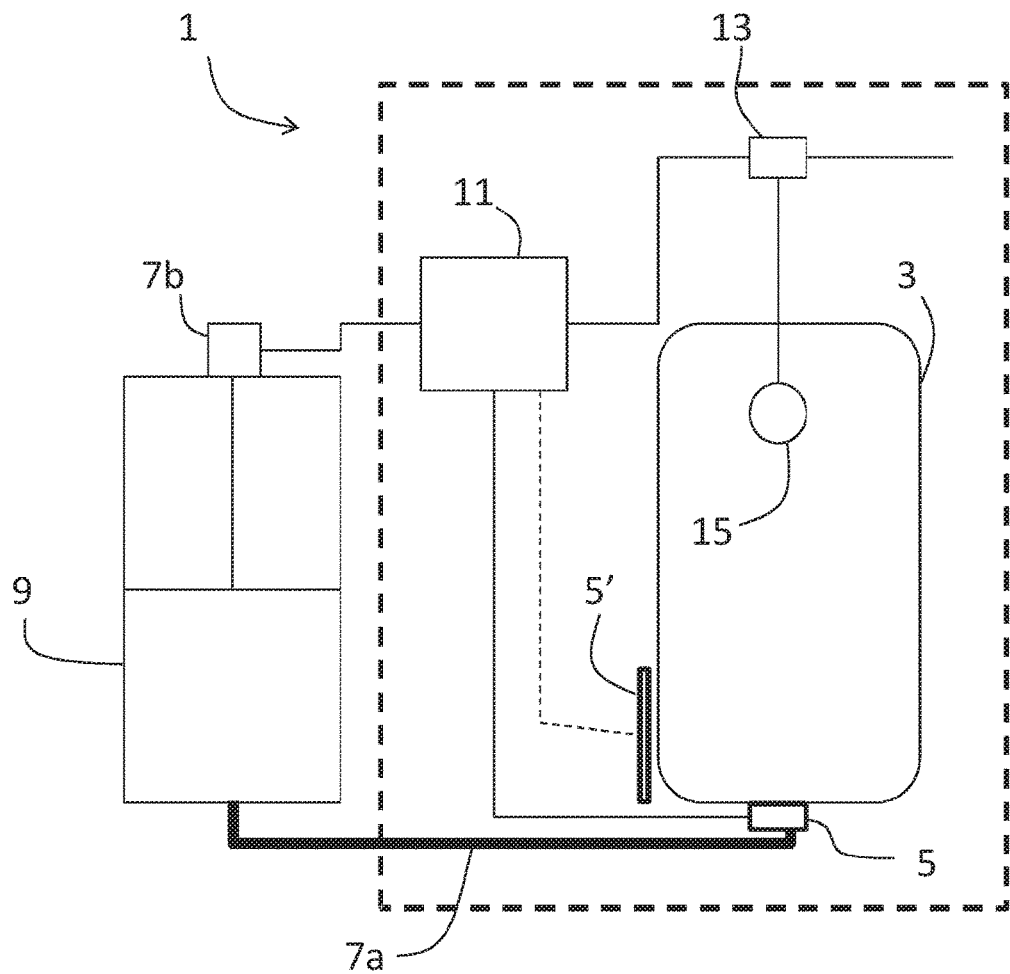
FIG. 1 is a schematic diagram of a slurry tank system connected to a chromatography column according to one embodiment of the invention.

FIG. 1 is a schematic view of a slurry tank system 1 connected to a chromatography column 9 according to one embodiment of the invention. The slurry tank system 1 comprises a slurry tank 3 which comprises a chromatography media slurry. The slurry tank system 1 comprises further a monitoring means 5, 5'. In this schematic view two different possible positions for the monitoring means 5, 5' is shown. The monitoring means 5 could be for example a weight measuring means 5. A weight measuring means would typically be positioned in connection with and below the slurry tank 3 in order to be able to measure the weight of the slurry tank. The monitoring means 5 could in another embodiment be an air sensor 5. This air sensor would suitably be positioned at the outlet from the slurry tank for measuring when air is starting to come with the slurry, i.e. when the slurry tank 3 is almost empty. In another embodiment the monitoring means 5' could be a level sensor 5' for example using ultrasonic or spectroscopic measuring for detecting the slurry level in the slurry tank 3.

The slurry tank system 1 further comprises a transferring tube 7a adapted to transfer slurry from the slurry tank 3 to the chromatography column 9. The transferring tube 7a is connected to an outlet of the slurry tank 3 and to a slurry inlet of the column 9. The transferring tube 7a is controlled by a transferring control means 7b. This could be a motor that controls the adaptor in the column. Slurry is in this example sucked into the column through a bottom valve when the adaptor is raised inside the column. A transferring control means 7b could in another embodiment be a pump provided along the transferring tube 7a or a means for providing a pressure into the slurry tank in order to push out slurry through the transferring tube 7a and into the column 9.

Furthermore the slurry tank system comprises a control system 11. This control system 11 is connected to both the monitoring means 5,5' and to the transferring control means 7b. The control system 11 is arranged to control the transferring of the slurry to the column in dependence of the content of slurry in the slurry tank 3. The control system 11 receives information from the monitoring means 5,5' about the content of slurry in the slurry tank 3. The control system 11 is preprogramed with for example different threshold levels for the content of slurry and programs for the transferring between these different threshold levels. For example the transferring speed can in one embodiment be lower after one specific threshold level has been reached. Or the transferring speed can be decreasing according to a predefined formula, for example linearly, starting from a predefined threshold level of the slurry content, i.e. when the slurry content is measured to decrease below the threshold level the transferring speed will decrease according to the formula. Further threshold levels could also be provided. One threshold level should trigger the transferring to stop completely.

In one embodiment of the invention the slurry tank system 1 further comprises a rinsing control means 13 connected to the control system 11 and adapted to control a rinsing of the slurry tank 3. The rinsing is primarily in purpose to rinse the inside walls of the slurry tank 3 in order to be able to use and transfer all the slurry efficiently to the column. The rinsing control means 13 is in one embodiment connected to a spray ball 15 provided inside the slurry tank 3. The spray ball can spray liquid or gas to the inside walls of the slurry tank 3 such that the slurry remaining on the walls will come down to the bottom of the slurry tank 3. The liquid could be for example water or packing buffer and the gas could be for example air or helium. Another alternative for rinsing the slurry tank would be to shake the whole tank, i.e. the rinsing control means 13 could be connected to some kind of vibrating means adapted to vibrate the slurry tank such that slurry remaining on the inside walls of the slurry tank will come down to the bottom of the tank. Suitably this rinsing of the slurry tank 3 will be provided when the content of slurry in the slurry tank 3 has been detected by the monitoring means 5, 5' to be below a predefined threshold level.

In one embodiment of the invention the added liquid will be measured such that any slurry dilution can be kept in mind. An alternative when liquid is added is to continually measure the slurry concentration. When a threshold concentration is reached the transferring of slurry to the chromatography column is terminated. The concentration measurement method could be Raman spectrometer or ultrasound.

Figure 2:
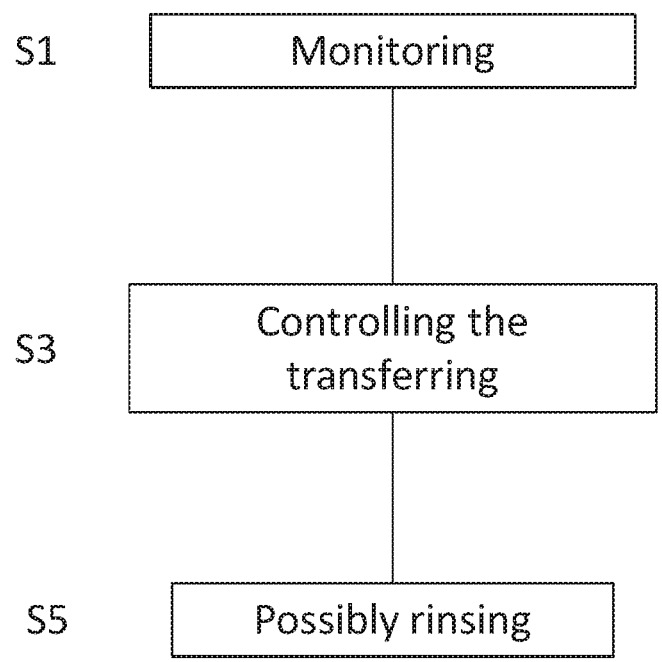
FIG. 2 is a flow chart describing a slurry transferring method according to one embodiment of the invention.

FIG. 2 is a flow chart describing a slurry transferring method according to one embodiment of the invention. The steps of the method will be described in order below:

S1: Monitoring the content in a slurry tank 3. In one embodiment the monitoring is done by measuring the weight of the tank. Another alternative is to measure the level in the tank by for example ultrasonic or resistance.

S3: Controlling the transferring of the slurry to the column in dependence of the content of slurry in the slurry tank. This can in one embodiment be provided by using predefined threshold levels whereby the transferring speed is decreased or stopped or varied when a specific threshold level has been reached, i.e. when the slurry content in the slurry tank is below a specific threshold level.

S5: Possibly rinsing the inside walls of the slurry tank 3 when the content of slurry in the slurry tank has been measured to be below a specific threshold level. The rinsing can be accomplished by for example spraying a liquid or a gas onto the inside walls or alternatively the slurry tank could be vibrated such that remaining slurry on the walls will come down to the bottom of the tank.

What is claimed is:

1. A method for transferring chromatography media slurry from a slurry tank to a chromatography column, said method comprising,
    monitoring the content of slurry in the slurry tank during the transferring and adjusting without stopping the speed of the transferring of the slurry to the column in dependence of the content of slurry in the slurry tank, using a control system, wherein the slurry transfer leaves at least some slurry remaining on the wall of the slurry tank forming a leftover slurry,
    using a collecting control collecting the leftover slurry into the remaining contents of the slurry tank to form a remaining slurry,
    monitoring the content of the remaining slurry,
    transferring the remaining slurry to the chromatography column, and
    terminating the remaining slurry transfer based on the content of the remaining slurry.

2. The method of claim 1, further comprising receiving the slurry content information in the control system and controlling the transferring of the slurry to the column from the control system.

3. The method of claim 1, further comprising stopping the transferring of slurry when the slurry content is below a predefined threshold level.

4. The method of claim 1, wherein the adjusting the speed of transferring comprises decreasing the transferring speed when the slurry content is below a predefined threshold level.

5. The method of claim 1, wherein the collecting step comprising vibrating the slurry tank to dislodge the leftover slurry.

6. The method of claim 1, wherein the collecting step comprising spraying a liquid or a gas into the slurry tank to collect the leftover slurry when the slurry content is below a predefined threshold level.

7. The method of claim 1, wherein the monitoring comprises measuring slurry level in the slurry tank or measuring weight of the slurry tank.

8. The method of claim 1, wherein the monitoring comprises measuring air content in a transferring tube used for the transferring of the slurry from the slurry tank to the chromatography column.

9. The method of claim 1, wherein the slurry is transferred to the chromatography column by raising an adaptor in the chromatography column.

10. The method of claim 1, wherein the content of the remaining slurry is monitored by measuring the amount of rinsing liquid added or continually measuring the concentration of the remaining slurry.

11. A slurry tank system comprising
    a slurry tank comprising a chromatography media slurry, wherein when the slurry is transferred, at least some slurry remains on the wall of the slurry tank forming a leftover slurry,
    a monitor monitoring the slurry content in the slurry tank,
    a transferring tube and a transfer control transferring slurry from the slurry tank to a chromatography column,
    a control system connected to the monitor and the transfer control, wherein the control system is arranged to adjust without stopping the transferring speed of the slurry to the column in dependence of the content of slurry in the slurry tank, and
    a collecting control connected to the control system to collect the leftover slurry forming a remaining slurry, the content of the remaining slurry is monitored and the remaining slurry is transferred to the chromatography column and the transfer is terminated based on the content of the remaining slurry.

12. The slurry tank system of claim 11, wherein the leftover slurry is collected through rising the inside walls of the slurry tank such that leftover slurry will come down to the bottom of the tank.

13. The slurry tank system of claim 11, wherein a collecting control starts collecting when the slurry content is below a predefined threshold level.

14. The slurry tank system of claim 11, wherein the collecting control controls a spray ball to spray liquid or gas to the inside walls of the slurry tank to collect the leftover slurry.

15. The slurry tank system of claim 11, wherein the control system further is arranged to stop the transferring of slurry when the slurry content is below a predefined threshold level.

16. The slurry tank system of claim 11, wherein the control system is arranged to decrease the transferring speed when the slurry content is below a predefined threshold level.

17. The slurry tank system of claim 11, wherein the monitor is arranged to measure slurry level in the slurry tank or weight of the slurry tank.

18. The slurry tank system of claim 11, wherein the monitor is arranged to measure air content in the transferring tube.

19. The slurry tank system of claim 11, wherein the control system further is arranged to control the transferring of slurry from the slurry tank to the chromatography column by raising an adaptor in the chromatography column.

20. The slurry tank system of claim 11, wherein the content of the remaining slurry is monitored by measuring the amount of rinsing liquid added or continually measuring the concentration of the remaining slurry.

21. A control system connected to a monitor to monitor the slurry content in a slurry tank, said control system further being connected to (1) a transfer control to adjust without stopping the speed of the transfer in a transfer tube between the slurry tank and a chromatography column and (2) a collecting control to collect slurry remaining on the wall of the slurry tank after the transfer to form a remaining slurry and the content of the remaining slurry is monitored and the remaining slurry is transferred to the chromatography column and the transfer is terminated based on the content of the remaining slurry, whereby said control system is arranged to adjust the speed of the transferring of the slurry to the column in dependence of the content of slurry in the slurry tank.

22. The control system of claim 21, wherein the control system is further arranged to stop the transferring of slurry when the slurry content is below a predefined threshold level.

23. The control system of claim 21, wherein the control system is arranged to decrease the transferring speed when the slurry content is below a predefined threshold level.

24. The control system of claim 21, wherein the collecting control collects by rinsing the inside walls of the slurry tank such that remaining slurry will come down to the bottom of the tank, wherein the collecting control is arranged to control the rinsing of the slurry tank to start rinsing when the slurry content is below a predefined threshold level.

25. The control system of claim 21, wherein the content of the remaining slurry is monitored by measuring the amount of rinsing liquid added or continually measuring the concentration of the remaining slurry.

* * * * *